United States Patent

Sossin et al.

(10) Patent No.: US 10,079,078 B2
(45) Date of Patent: Sep. 18, 2018

(54) METHOD FOR CORRECTING A SPECTRUM

(71) Applicant: Commissariat a l'energie atomique et aux energies alternatives, Paris (FR)

(72) Inventors: Artur Sossin, Grenoble (FR); Veronique Rebuffel, Corenc (FR); Joachim Tabary, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 166 days.

(21) Appl. No.: 15/288,146

(22) Filed: Oct. 7, 2016

(65) Prior Publication Data

US 2017/0103822 A1 Apr. 13, 2017

(30) Foreign Application Priority Data

Oct. 9, 2015 (FR) ...................... 15 59646

(51) Int. Cl.
| | | |
|---|---|---|
| *G01N 23/20* | (2018.01) | |
| *G21K 1/10* | (2006.01) | |
| *G01N 23/083* | (2018.01) | |
| *A61B 6/00* | (2006.01) | |

(52) U.S. Cl.
CPC .............. *G21K 1/10* (2013.01); *A61B 6/4035* (2013.01); *G01N 23/083* (2013.01)

(58) Field of Classification Search
None
See application file for complete search history.

(56) References Cited

U.S. PATENT DOCUMENTS

| | | | |
|---|---|---|---|
| 2012/0140891 A1 | 6/2012 | Tabary et al. | |
| 2012/0263275 A1* | 10/2012 | Harding | G01N 23/20 378/71 |
| 2014/0247920 A1* | 9/2014 | Marks | G01N 23/20008 378/87 |
| 2014/0286478 A1* | 9/2014 | Paulus | G01N 23/20 378/88 |

OTHER PUBLICATIONS

French Preliminary Search Report dated Aug. 22, 2016 (with Written Opinion) in French Application 15 59646 filed on Oct. 9, 2015(with English Translation of Categories of Cited Documents).

(Continued)

*Primary Examiner* — Hoon Song
(74) *Attorney, Agent, or Firm* — Oblon, McClelland, Maier & Neustadt, L.L.P.

(57) ABSTRACT

The invention relates to a method for processing energy spectra of a radiation transmitted by an object irradiated by a source of ionizing radiations, in particular an X radiation, for applications in medical imaging or non-destructive inspection. The method implements a detector comprising a plurality of pixels, each pixel being able to establish a spectrum of the radiation transmitted by the object. The method makes it possible, from a plurality of spectra detected, to establish so-called corrected spectra. Each corrected spectrum is an estimation of the spectrum of a radiation, called primary radiation, transmitted by the object. The invention makes it possible to reduce the influence of the scattering, by the object, of the spectrum emitted by the source.

17 Claims, 9 Drawing Sheets

(56) References Cited

OTHER PUBLICATIONS

Kai Yang, et al., "A breast-specific, negligible-dose scatter correction technique for dedicated cone-beam breast CT: a physics-based approach to improve Hounsfield Unit accuracy", Physics in Medicine & Biology, vol. 59, (21), 2014, 19 pgs.

A. Sossin, et al., "Fast scattering simulation tool for multi-energy x-ray imaging", Nuclear Instruments and Methods in Physics Research A, vol. 802, (9), 2015, 7 pgs.

* cited by examiner

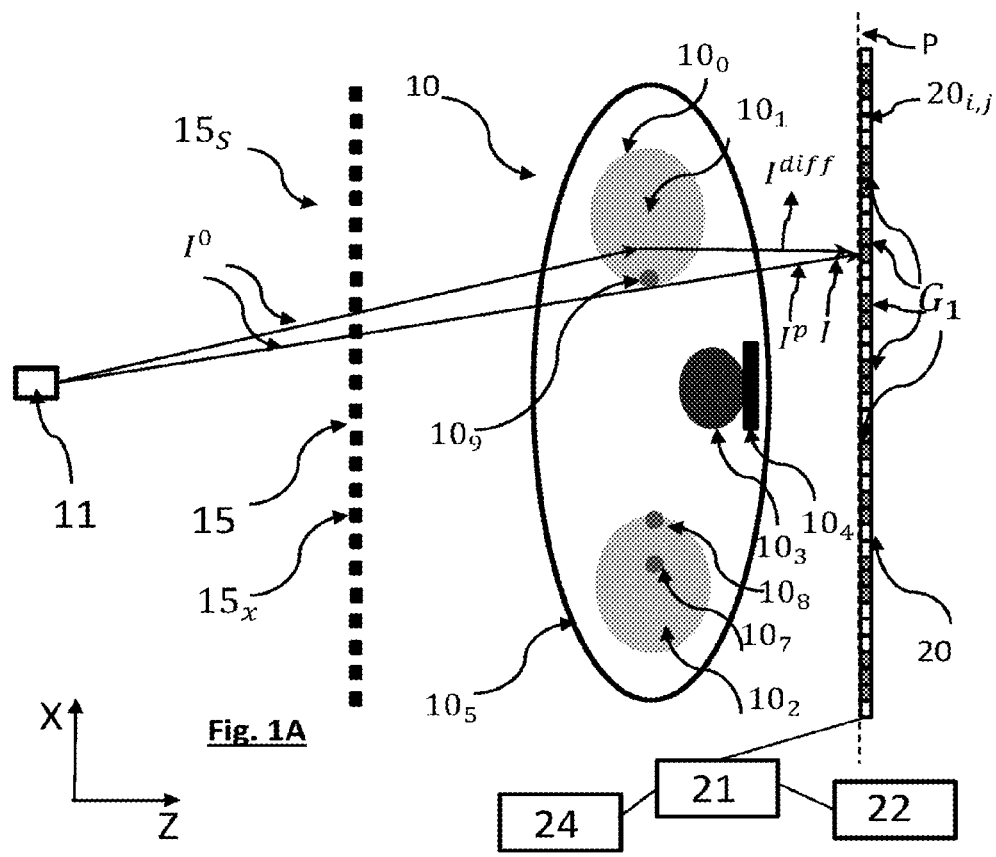
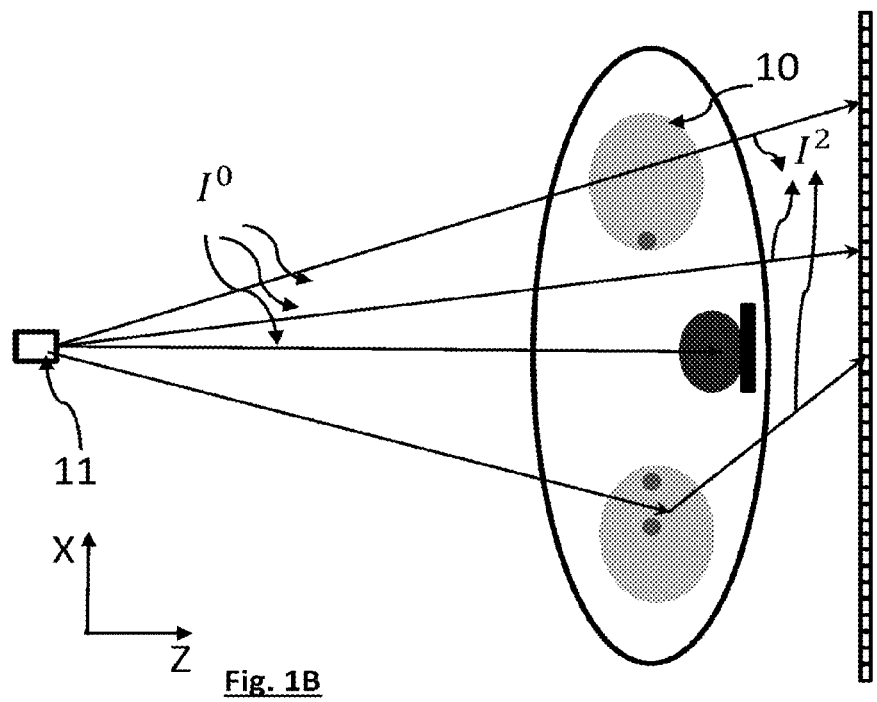

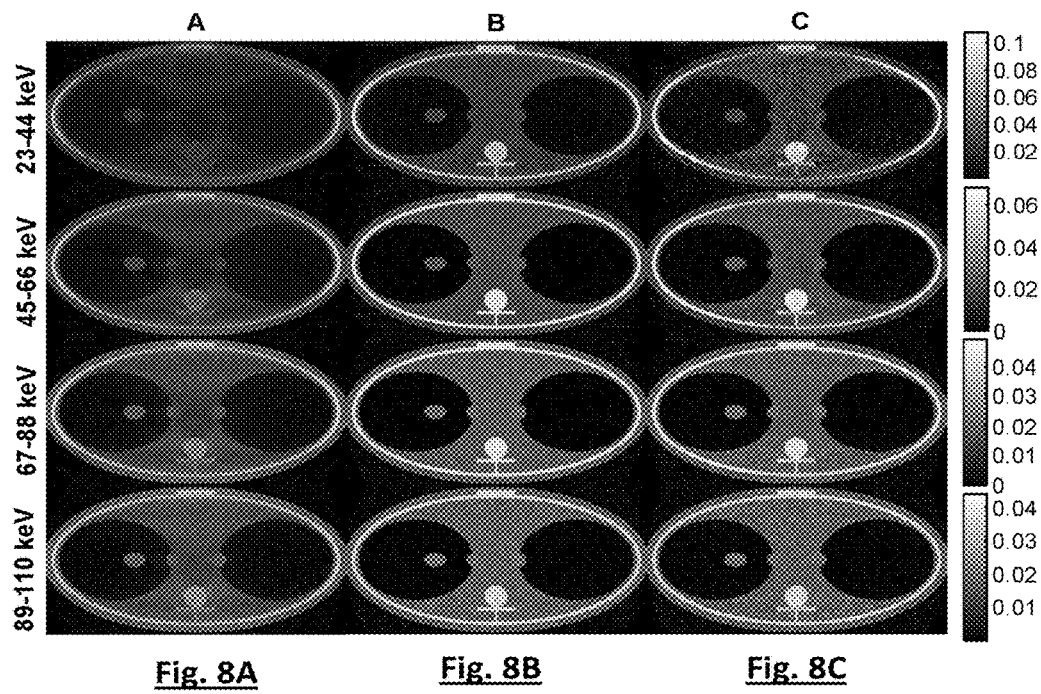
Fig. 8A    Fig. 8B    Fig. 8C
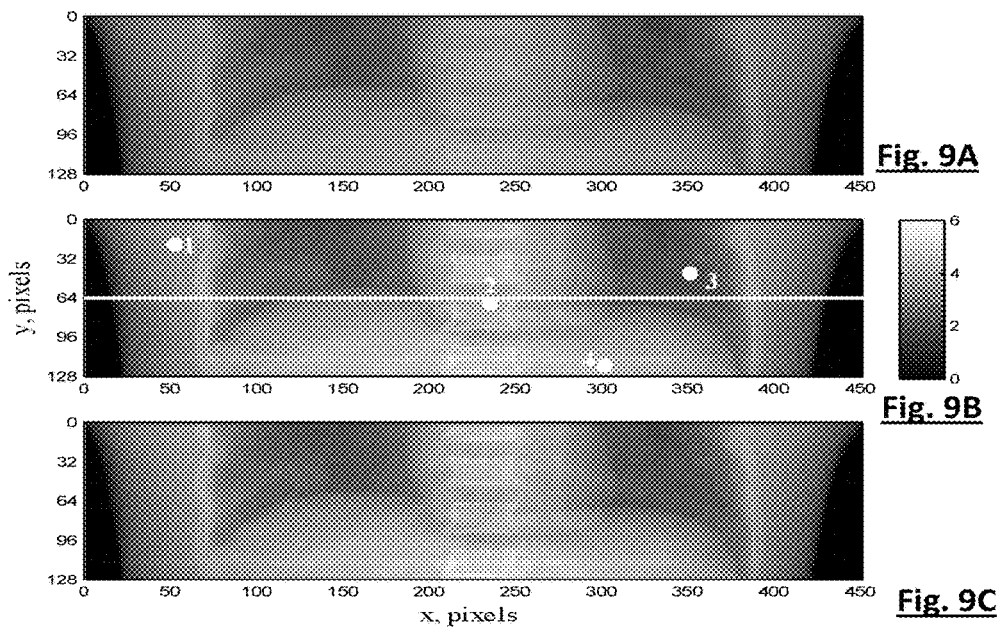
Fig. 9A
Fig. 9B
Fig. 9C

METHOD FOR CORRECTING A SPECTRUM

TECHNICAL FIELD

The technical field of the invention is the processing of spectra of a radiation transmitted by an object, the latter being irradiated by a source of ionizing radiation, in particular an X radiation. The aim of the invention is to obtain a plurality of spectra using a pixelated detector, and to perform a correction of all or some of the spectra, so as to limit the influence of a component representative of a scattered radiation. The applications are for use in medical imaging or in non-destructive inspection.

PRIOR ART

The inspection of objects by X radiation, in the medical or industrial field, is very widely used. The existing methods consist in arranging an object between a source of radiation and a detector, then in irradiating the object using the source. The detector then forms an image, generally in two dimensions, of the radiation transmitted by the object. This image is representative of the attenuation, by the object, of the radiation emitted by the source.

The radiation transmitted by the object generally comprises a component resulting from the scattering, by the object, of the radiation emitted by the source. It is all the more significant when the energy of the radiation is weak and/or the object consists of materials with a high atomic number. This component, commonly called scattering radiation, perturbs the interpretation of the images, because it is only indirectly linked to the attenuation by the object. Furthermore, whereas the non-scattered radiation, called primary radiation, is propagated between the source and the detector along a rectilinear trajectory, the scattered radiation originates from any point of the object, and its trajectory, from this point of origin, is distributed according to different angles. It is therefore sought to estimate this scattering component, so as to extract it from the signal measured by the detector, prior to the processing of the images with a view to the interpretation thereof.

Numerous methods have been developed for trying to estimate and reduce the proportion of the scattered radiation in these images, so as to obtain an image essentially representative of the non-scattered radiation, called primary radiation, propagated between the source and the object in a rectilinear direction.

For example, the publication by Zhu L entitled "Scatter Correction Method for X-ray CT Using Primary Modulation: Theory and Preliminary Results", IEEE Transactions on Medical Imaging, Vol. 25, No. 12, December 2006, describes a method consisting in interposing a removable mask, taking the form of a grid, between a source of X rays and an object. This publication is based on the fact that such a mask generates a significant spatial modulation of the primary radiation, in high spatial frequencies, whereas its influence on the scattered radiation, in the low spatial frequencies, is less significant. Thus, in a frequency space, it is possible to establish a discrimination between the primary radiation and the scattered radiation.

Moreover, the publication by Ning R, entitled "X-ray Scatter Correction Algorithm for Cone Beam CT-Imaging", Med. Phys. 31 (5), May 2004, also describes a method consisting in interposing a removable mask between a source of X rays and an object. The mask allows for an attenuation such that, when it is arranged between the source and the object, the radiation measured by the detector is considered to be representative of only the scattered radiation. In other words, this mask allows for an attenuation, considered to be total, of the primary radiation.

The current detectors make it possible to obtain images in two dimensions with a quality that never ceases to improve. One recent trend is the emergence of detectors allowing the acquisition of spectral images, that is to say of images according to different energy bands. These detectors, often based on semiconductor detectors having a spectrometric function, add a spectral dimension to the data acquired, the latter being generally obtained in two dimensions. It is then possible to obtain an image of the radiation transmitted by the object according to different energy bands.

Now, the abovementioned methods do not relate to spectral imaging. The inventors propose an alternative solution, based on spectral imaging, allowing for an effective correction of the radiation detected by the detector, so as to extract the primary radiation therefrom, and do so simultaneously in several energy bands. The tests described at the end of the description testify to the effectiveness of the method.

SUMMARY OF THE INVENTION

The invention is a method for correcting a spectrum of an ionizing electromagnetic radiation transmitted by an object, according to any one of the attached claims. More precisely, an object of the invention is a method for correcting a spectrum of an ionizing electromagnetic radiation transmitted by an object, the object being arranged between an irradiation source and a detector, the irradiation source being able to emit an ionizing electromagnetic radiation, called incident radiation, towards said object;

the detector comprising pixels, each pixel being able to detect a radiation transmitted by the object towards the detector, and to acquire a spectrum therefrom, the transmitted radiation comprising a scattering radiation, caused by the scattering of the incident radiation in the object, and a primary radiation;

the method comprising the following steps:

a) interposing a mask between the source and the object, and acquiring, by several pixels, a first spectrum of a first radiation transmitted by the object, the mask comprising attenuating elements, configured to attenuate a part of said incident radiation, and of which a projection on the detector defines a first group of pixels;

b) obtaining, for each pixel of the first group of pixels, a second spectrum of a second radiation transmitted by the object to the detector, in the absence of said mask;

c) comparing, for each pixel of said first group of pixels, the first spectrum and the second spectrum, so as to obtain a comparison spectrum;

d) at each pixel of the first group of pixels, applying a transition matrix, previously established, to said comparison spectrum, to obtain an estimation of a so-called primary spectrum representing the primary radiation transmitted by the object to said pixel, and estimating a scattering spectrum, representative of the scattering radiation transmitted by the object;

e) for all or some of the pixels of the detector, from each scattering spectrum estimated in the step d), correcting the second spectrum or the first spectrum, so as to obtain a corrected spectrum.

The mask is preferably interposed between the radiation source and the object.

According to an embodiment:
the step a) is implemented in a plurality of configurations, each configuration having associated with it a position of the detector and of the source relative to the object, so as to obtain, in each configuration and for each pixel, a first spectrum, each configuration also having associated with it a first group of pixels;
the step b) comprises, for all or some of the pixels of the first group associated with a configuration, a determination of a second spectrum from a first spectrum obtained according to another configuration.

That avoids using a removable mask. The fact that pixels belong to a first group of pixels according to one configuration, and do not belong to the first group of pixels associated with said other configuration, and are then directly exposed to the source of radiation, is then exploited. The radiation that they receive, according to this other configuration, is considered to be representative of the radiation that they would receive, in said configuration, in the absence of the mask.

According to this embodiment, each configuration has associated with it a parameter, such that at least one second spectrum according to a configuration associated with a first parameter is obtained from a first spectrum obtained according to another configuration associated with a second parameter, different from the first parameter. This parameter can be the angle of inclination of the source and/or of the detector relative to the object.

According to one embodiment, called tomographic embodiment, the steps a) to e) are implemented according to a plurality of configurations, each configuration having associated with it a position of the detector and of the source relative to the object, so as to obtain, in each configuration, for a plurality of pixels, a corrected spectrum, the corrected spectra of each configuration being used to produce a tomographic reconstruction of the object. That makes it possible to apply the invention to a tomographic reconstruction.

Another subject of the invention is an information storage medium, comprising instructions for the execution of a method as described in this application, these instructions being able to be executed by a microprocessor.

Another subject of the invention is a device for producing images of an object, comprising:
an irradiation source, able to emit an ionizing electromagnetic radiation, called incident radiation, towards said object;
a detector comprising pixels, each pixel being able to detect a radiation transmitted by the object towards the detector, and to acquire a spectrum therefrom;
a mask, able to be interposed between the source and the object, the mask comprising attenuating elements, configured to attenuate a part of the incident radiation, and of which a projection onto the detector defines a first group of pixels;
a processor, able to receive spectra detected by each pixel, and to implement steps c) to e) of the method as described in this specification.

The invention will be better understood from the exemplary embodiments described hereinbelow, which are based on the following figures.

FIGURES

FIGS. 1A and 1B represent a device allowing for the implementation of the invention.

Figure 4A:
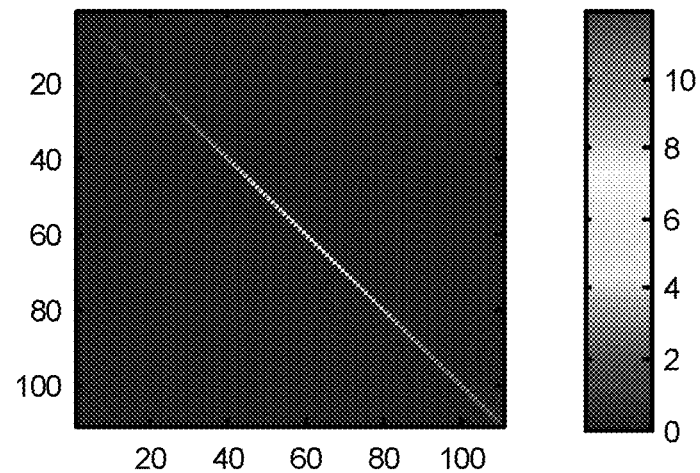
Figure 4B:
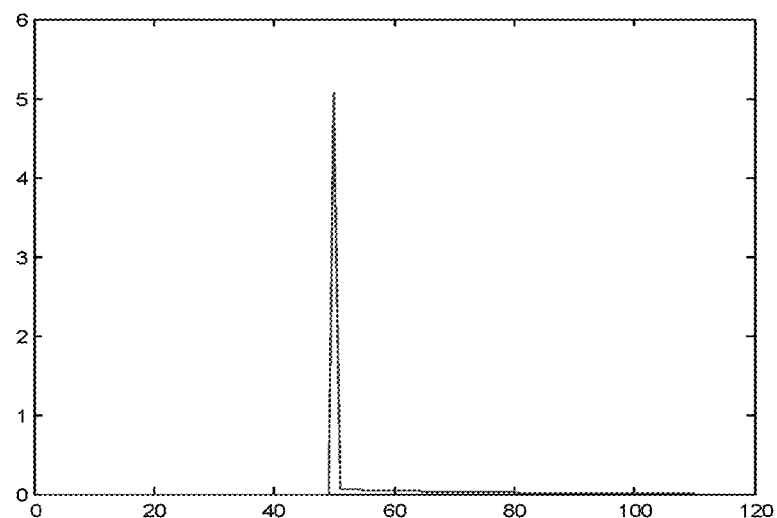
Figure 4C:
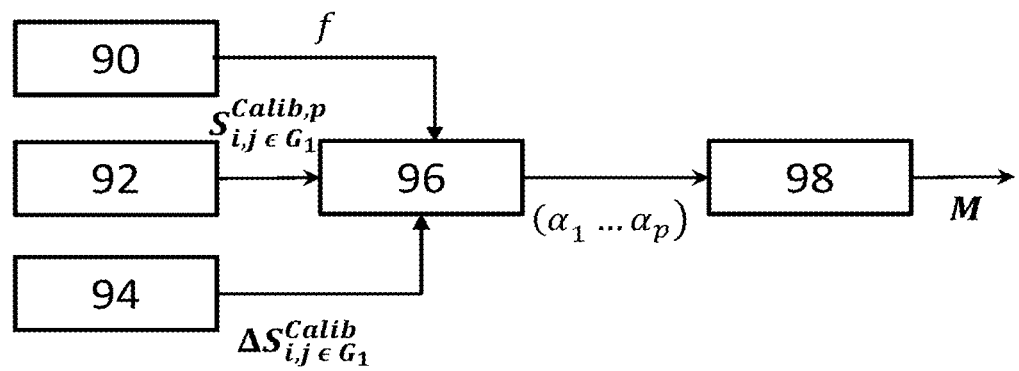

FIG. 4A represents a transition matrix implemented in the invention. FIG. 4B represents a column of this transition matrix. FIG. 4C represents the steps of a method making it possible to obtain this transition matrix.

Figure 5A:
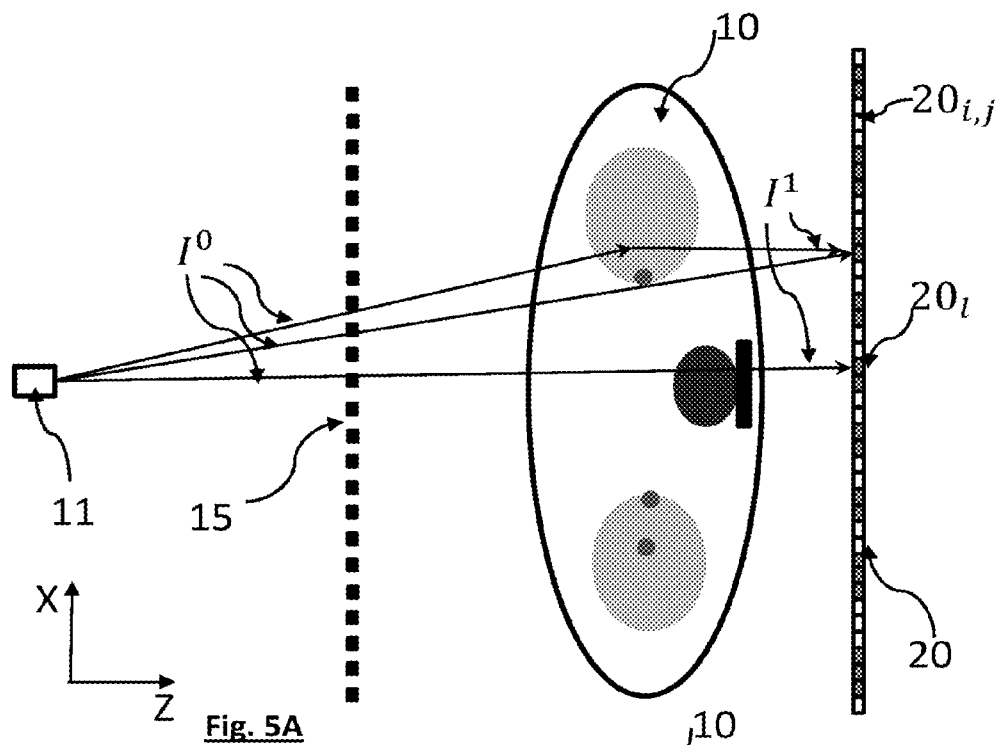
Figure 5B:
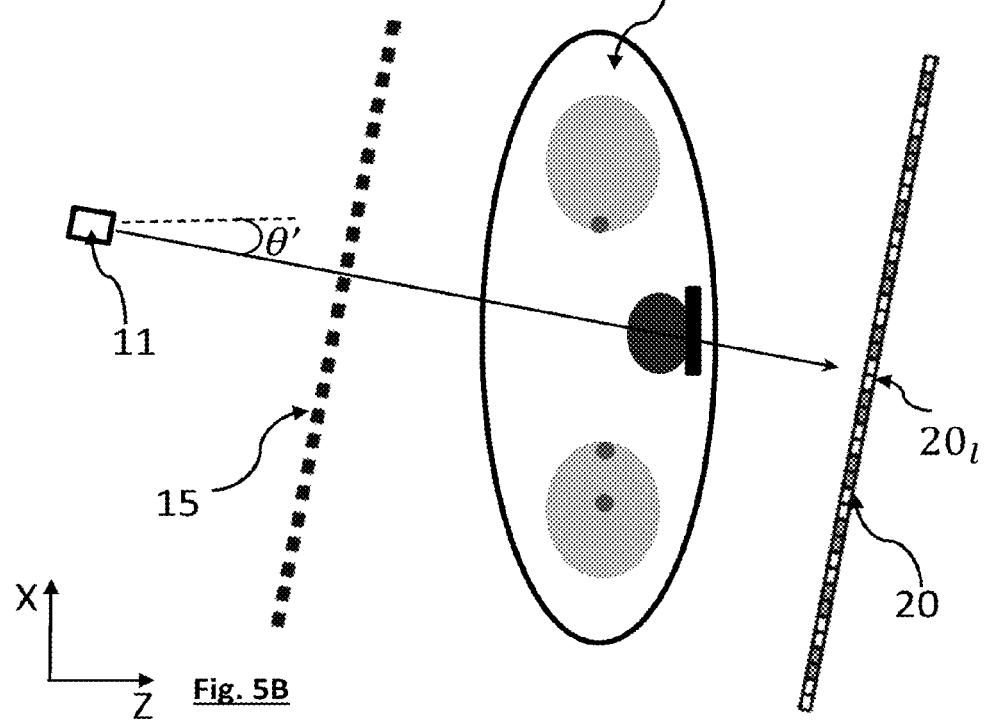

FIGS. 5A and 5B represent an embodiment of the invention suitable for a tomographic reconstruction of an object.

Figure 6A:
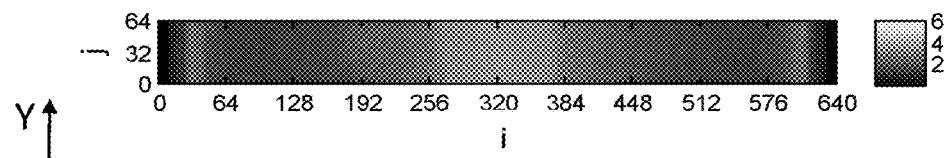
Figure 6B:
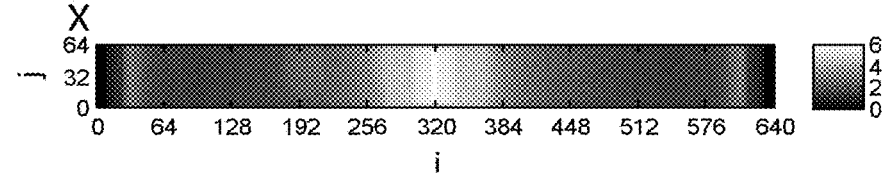
Figure 6C:
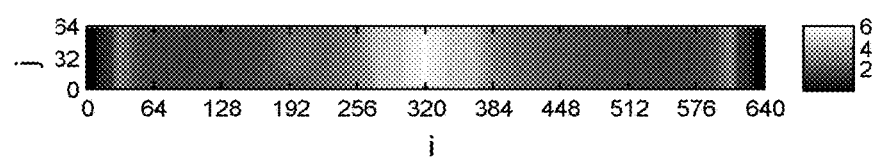
Figure 6D:
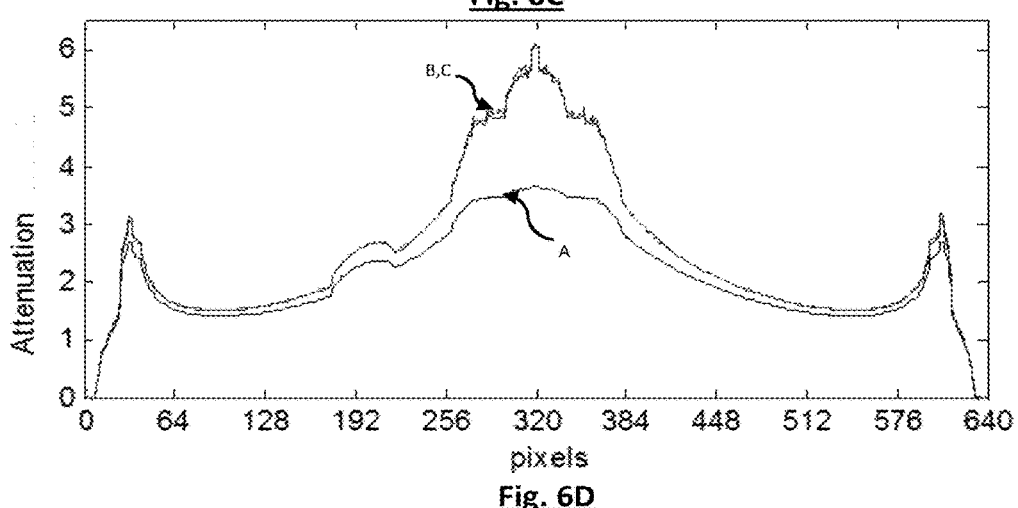

FIGS. 6A, 6B and 6C represent results of modelling simulating an image of an object, each image being based on spectra measured by the pixels of a detector, these spectra respectively representing the total radiation, the primary radiation and the estimation of the primary radiation according to the invention. FIG. 6D represents a horizontal profile of each of FIGS. 6A, 6B and 6C.

FIGS. 7A, 7B, 7C and 7D represent spectra of the total radiation, of the primary radiation and of the primary radiation estimated according to the invention, measured by different pixels of the detector.

FIGS. 8A, 8B and 8C represent modelling of a tomographic reconstruction, in different energy ranges, the tomographic reconstruction being respectively produced on the basis of the total radiation, of the primary radiation and of the estimation of the primary radiation according to the invention.

Figure 9D:
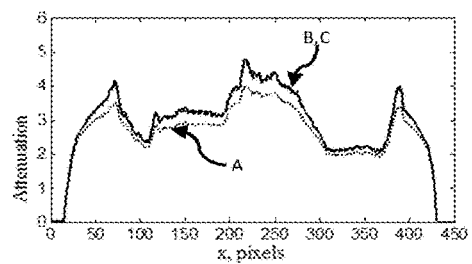
Figure 10A:
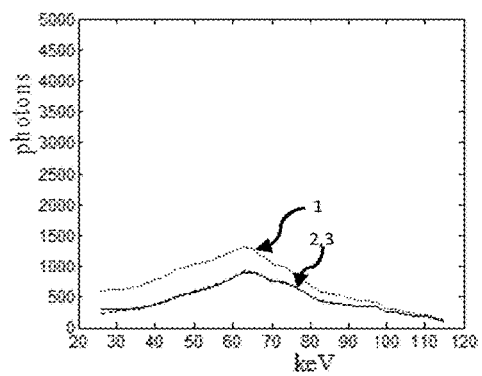
Figure 10B:
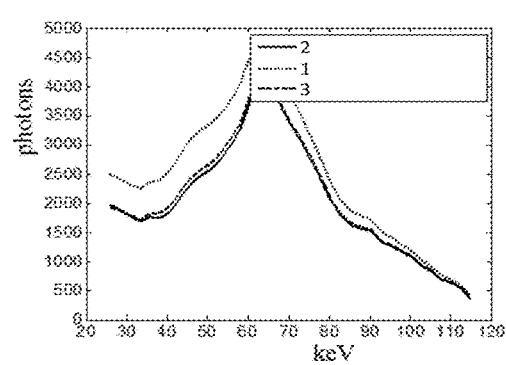
Figure 10C:
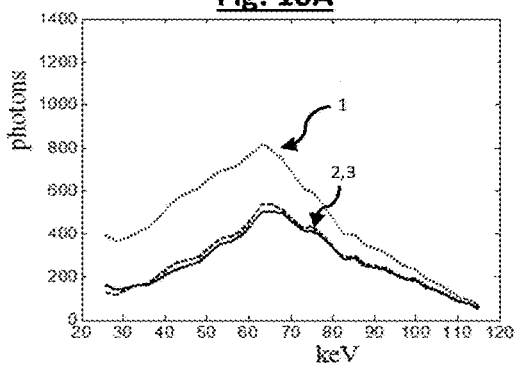
Figure 10D:
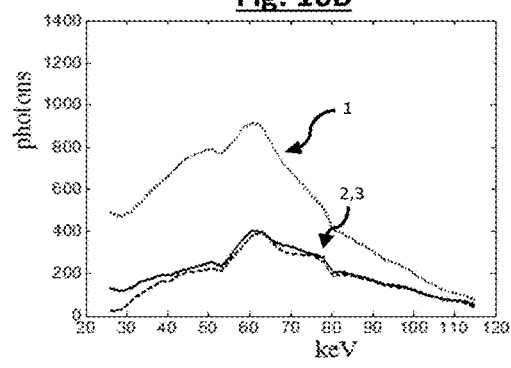

FIGS. 9A, 9B and 9C represent images of experimental measurements performed on a phantom, each image being based on spectra measured by the pixels of a detector, these spectra respectively representing the total radiation, the primary radiation estimated according to a reference method and the estimation of the primary radiation according to the invention. FIG. 9D shows profiles along a horizontal line represented in FIG. 9B.

FIGS. 10A, 10B, 10C and 10D show energy spectra of the total radiation, of the primary radiation estimated according to a reference method and of the primary radiation as obtained according to the invention, these spectra corresponding to the four points represented in FIG. 9B.

SUMMARY OF PARTICULAR EMBODIMENTS

FIG. 1A represents an embodiment of a device 1 implementing a method according to the invention.

An irradiation source 11 emits an ionizing electromagnetic radiation $I^0$, called incident radiation, towards an object 10. The object 10 is arranged between the irradiation source 11 and a radiation detector 20. The radiation detector is a detector comprising pixels $20_{i,j}$ arranged on a plane, called detection plane P. The indices i,j designate the coordinates of each pixel in the detection plane. The pixels can extend in a row but, generally, they extend according to a regular two-dimensional matrix.

The object 10 can be a living biological tissue, for example a part of the body of an animal or of a human being. The device is then a medical imaging device. The object can also be an industrial part or luggage, the device then being used for non-destructive inspection purposes. In this example, the object is a part of a phantom of a human body, comprising a matrix $10_0$, two lungs $10_1$, $10_2$, a spinal column $10_3$, a vertebra $10_4$, dimensions $10_5$ and tumours $10_7$, $10_8$ and $10_9$.

The term ionizing electromagnetic radiation designates an electromagnetic radiation consisting of photons of energy higher than 1 keV, and preferably lower than 5 MeV. The energy range of the ionizing radiation can lie between 1 keV and 2 MeV, but it more often than not extends between 1 keV and 150 keV or 300 keV. The ionizing radiation can be an X or a γ radiation. Preferably, the ionizing radiation source is poly-energetic, the incident radiation being emitted according to an energy range extending generally across several tens or even hundreds of keV. It is notably an X-ray emitting tube.

A portion of the photons, forming the incident radiation $I^0$, pass through the object and reach the detector 20, without interacting with the object. These photons form a primary component, or primary radiation $I^p$. Other photons forming the incident radiation $I^0$ are attenuated in the object, for example by photoelectric effect. Finally, some photons undergo a scattering interaction in the sample, of Compton inelastic scattering or Rayleigh elastic scattering type. The scattering, whether inelastic or elastic, generates a change in the direction of the photon.

Thus, the object 10 irradiated by the source 11 transmits to the detector 20 a radiation I, called transmitted radiation, comprising:
- a direct component, or primary radiation, $I^p$, not having interacted with the object, and the trajectory of which from the source is rectilinear;
- a scattering component $I^{diff}$, or scattering radiation, due to a scattering of the incident radiation in the object.

The radiation I transmitted by the object reaches the pixels of the detector 20, each pixel detecting a portion of this radiation. The radiation transmitted by the object and detected by a pixel $20_{i,j}$ is denoted $I_{i,j}$.

As described in relation to the prior art, the scattering radiation $I^{diff}$ perturbs the interpretation of the measurements. In effect, contrary to the primary radiation $I^p$, the scattering radiation is propagated from the object towards the detector, in a variable direction. Thus, a portion of the radiation collected by each pixel $20_{i,j}$ of the detector does not originate directly from the radiation source 11, but results from the scattering phenomenon. The interpretation of the images is usually based on the attenuation of the incident radiation by the detector, the latter being obtained by a ratio, over a given energy range, of the intensity of the primary radiation $I^p$ to the intensity of the incident radiation $I^0$. A good interpretation of the images presupposes the knowledge of the intensity of the primary radiation $I^p$, whereas the radiation I transmitted by the object, and measured by the detector, comprises a sum of said primary radiation $I^p$ and of the scattered radiation $I^{diff}$.

Each pixel $20_{i,j}$ constitutes a radiation detector, comprising:
- a detector material, capable of interacting with the photons of the radiation I transmitted by the object, this material being of scintillator type or, preferably, a semiconductive material compatible with a use at ambient temperature, of CdTe, CdZnTe type;
- an electronic circuit, capable of generating a signal whose amplitude depends on, and is preferably proportional to, the energy deposited by each photon interacting in the detector material;
- a spectrometry circuit, capable of establishing a spectrum, denoted $S_{i,j}$ of energy of the signals detected during a time period, called acquisition period.

Thus, when the pixels are arranged regularly in a matrix arrangement, each pixel is capable of producing a spectrum $S_{i,j}$ of the radiation transmitted by the object. The detector is then capable of forming several images, each image representing a content of each spectrum in a determined energy range $\Delta E$. Typically, each image comprises the integral or the mean value of each spectrum $S_{i,j}$ in said energy band. The term spectral imaging then applies, since the detector is both spatially and spectrally resolved.

Also, under the effect of the irradiation by the incident radiation $I^0$, the object 10 transmits a radiation I, called transmitted radiation, towards a pixelated spectrometric detector 20, of which each pixel $20_{i,j}$ is capable of detecting said transmitted radiation I and of forming an energy spectrum $S_{i,j}$ of the duly detected radiation $I_{i,j}$.

The term energy spectrum corresponds to a histogram of the amplitude of the signals detected during a period of acquisition of the spectrum. A relationship between the amplitude A and the energy E can be obtained by an energy calibration function g such that E=g(A), according to principles known to those skilled in the art. An energy spectrum $S_{i,j}$ is therefore a vector, of which each term $S_{i,j}(n)$ represents a quantity of radiation detected by the pixel $20_{i,j}$ in an energy range $$E \pm \frac{\partial E}{2},$$

with $\partial E$ being the spectral width of each channel.

Each energy spectrum $S_{i,j}$ can be considered to be a sum of a spectrum of the primary radiation, denoted $S_{i,j}^P$ and of a spectrum of the scattering radiation $S_{i,j}^{diff}$, to within a noise term. Also, $S_{i,j} \approx S_{i,j}^P + S_{i,j}^{diff}$ (1). The sign ≈ means an equality to within a noise term, this noise notably being able to result from the detector or from so-called stacking effects, occurring when two incident photons are detected simultaneously.

One objective of the invention is to correct the spectrum measured by each pixel, so as to reduce the scattering component $S_{i,j}^{diff}$ and establish a corrected spectrum $S_{i,j}^*$ such that $S_{i,j}^* \approx S_{i,j}^P$. In other words, the corrected spectrum $S_{i,j}^{diff}$ corresponds to an estimation $\hat{S}_{i,j}^P$ of the spectrum of the primary radiation reaching the pixel $20_{i,j}$: $S_{i,j}^* = \hat{S}_{i,j}^P$.

The device also comprises a mask 15, arranged between the source 11 and the detector 20, and in this example between the source 11 and the object 10, which constitutes the preferred configuration. This mask comprises attenuating elements $15_x$ distributed spatially on a surface $15_S$ on which the mask extends. Each attenuating element is capable of partially attenuating a portion of the incident radiation $I^0$ produced by the irradiation source. The attenuating elements are distributed discretely, such that the space between two adjacent attenuating elements is less attenuating than said attenuating elements. In other words, the attenuating elements define a discrete spatial distribution of attenuation coefficients $att_{15}^x$, $att_{15}^{x'}$ such that, between two adjacent attenuating elements $15_x$, $15_{x'}$, the attenuation coefficient $att_{15}^0$ is less than the attenuation coefficient $att_{15}^x$, $att_{15}^{x'}$ associated with each attenuating element.

The term attenuation coefficient is known to those skilled in the art. It can be expressed according to the expression $$att_{15}^x(E) = -\ln\left[\frac{I^x(E)}{I^0(E)}\right],$$

where $I^0(E)$ designates an intensity, with an energy E, of an incident radiation $I^0$ indent on the attenuating element $15_x$ and $I^x(E)$ designates an intensity, with said energy E of a radiation $I^x$ transmitted by the attenuating element $15_x$.

Generally, the interposition of the mask between the source and the detector should not significantly modify the scattering radiation originating from the detector, relative to a configuration without mask. Also, preferably, each attenuating element exhibits an attenuation coefficient, as previously defined, lying between 0.05 and 1.5, at one of the energies of the energy range according to which the incident radiation $I^0$ is emitted, or at the mean energy of this energy range. Thus, by disregarding the scattering, each attenuating element attenuates, preferably, between 5% and 80% of the incident radiation $I^0$ produced by the source and/or passing through the mask in the space extending between the attenuating elements of the mask. Preferably, the attenuation coefficient is less than 1, even less than 0.5, and preferably less than 0.3. Thus, each attenuating element respectively attenuates less than 60% or less than 40%, and preferably less than 30% of the radiation produced by the source, or of the radiation passing between the attenuating elements of the mask. Below an attenuation coefficient equal to 0.05, corresponding to an attenuation of 5% of the radiation produced by the source, the inventors consider that the attenuation is insufficient. In other words, the mask 15 therefore makes it possible to establish an attenuation contrast, between the attenuating elements $15_x$ and the space extending between said attenuating elements, the latter attenuating between 5% and 30%, even 40%, even more of the radiation passing through said space.

In addition or alternatively, it is possible to define a global attenuation of the mask 15 in the form of a product of a filling factor by the percentage of the incident radiation attenuated by the mask, the latter being determined at an energy of the energy range of the incident radiation $I^0$ emitted by the irradiation source 11, or at a mean energy of this range. The filling factor corresponds to a ratio of the surface area of the mask occupied by the set of attenuating elements $15_x$ to the total surface area of the mask. The global attenuation of the mask, thus defined, is preferably greater than 1% and less than 10%. Thus, a mask satisfying this condition can have a filling factor equal to 0.08, each element $15_x$ of the mask attenuating 10% of the incident radiation, which gives a global attenuation of the mask, as previously defined, equal to 0.08 (8%).

Each attenuating element can have any form but at least one dimension in a direction of the surface $15_S$ on which it extends, is less than 5 mm, and preferably less than 2 mm, even than 1 mm. In all of the embodiments previously described, the mask preferably extends on a plane XY parallel to a plane on which the pixels of the detector extend.

The spacing between two adjacent attenuating elements, on said mask, can be less than 5 mm, and preferably lies between 1 mm and 5 mm. Generally, the spacing between two adjacent attenuating elements, after projection onto the detector 20, advantageously lies between 1 and 10 cm, and preferably less than 5 cm or than 3 cm. As described hereinbelow, the projection of each attenuating element $15_x$ onto the detector defines an elemental shadow zone. Each elemental shadow zone extends around a central point. Advantageously, the spacing between the central points of two adjacent elemental shadow zones lies between 1 and 10 cm, and preferably lies between 1 cm and 5 cm. Projection should be understood to mean a projection in the direction of propagation of the radiation emitted by the source.

Figure 1C:
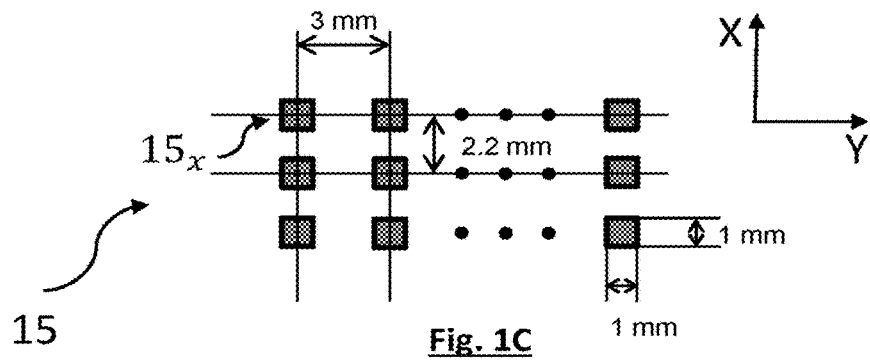
FIG. 1C represents a mask with which the device is equipped, also drawn in FIG. 1A.

An example of a mask is represented in FIG. 1C. Each attenuating element $15_x$ is a parallelepipedal block, the area of which, on the surface $15_S$ on which the mask extends, is 1 mm*1 mm, the spacing between the centre of each element $15_x$ being respectively 3 mm in a first direction Y and 2.2 mm in a second direction X at right angles to the first direction. In this example, the material forming the mask is aluminium, and its thickness is 2 mm, which corresponds to an attenuation coefficient of 0.9 to 100 keV, which results in 10% of the incident radiation being attenuated. The thickness extends in a direction at right angles to the surface on which the mask extends. Generally, the mask is produced according to a material that is sufficiently attenuating to attenuate a sufficient portion of the primary radiation. Excessively dense materials, of heavy metal type, for example lead, likely to produce a significant scattering of the incident radiation before the latter reaches the object, should however preferably be avoided. Preferred materials for the mask include aluminium, copper, graphite and boron.

Other geometries can be envisaged, by considering, for example, an irregular spacing between the different attenuating elements, or an irregular geometry of each attenuating element. A mask in grid form, defining meshes, is also possible, the attenuating elements being arranged between each mesh.

The surface $15_S$ on which the mask extends, between each attenuating element, preferably consists of a material considered to be transparent to photons, in the energy range considered. It can be a thin thickness of plastic, of paper or of a light metal, of aluminium, iron or copper type, or a space left free and occupied by air. Thus, between each attenuating element $15_x$, the attenuation coefficient, as previously defined, is preferably less than 0.5, even than 0.2 or even 0.1. Preferably, between each attenuating element, the attenuation coefficient is negligible.

The number of attenuating elements is dimensioned so as to cover the observation field of the detector. In the example described, the attenuating elements are distributed according to a matrix of 17 by 3 elements, or a total of 51 elements.

The mask can be removable or fixed. By having a removable mask, it becomes possible to produce spectrum acquisitions without the mask, as is represented in FIG. 1B.

When the mask is interposed between the source and the detector, its projection, onto the detector, in the direction of propagation of the incident radiation $I^0$, defines a shadow zone, grouping together the pixels of the detector $20_{i,j}^x$ aligned relative to each attenuating element $15_x$, in said direction of propagation. More specifically, as previously described, the projection of each attenuating element $15_x$, in the direction of propagation of the incident radiation, forms an elemental shadow zone on the detector. The set of the elemental shadow zones constitutes said shadow zone. The pixels of the shadow zone constitute a first group of pixels, denoted $G_1$. This first group $G_1$ can be determined previously either by computation or experimentally, without an object between the source and the detector. The pixels $20_{i,j \notin G1}^x$ not belonging to this first group receive a radiation not attenuated by the attenuating elements $15_x$, while each pixel $20_{i,j \in G1}^x$ belonging to this first group receives a radiation attenuated by an attenuating element $15_x$, the latter being situated on a line extending between said pixel and the irradiation source 11.

The device also comprises a computation unit, or processor 21, for example a microprocessor, which is capable of processing each spectrum $S_{i,j}$ measured by the pixels of the detector. In particular, the processor is a microprocessor linked to a programmable memory 22 in which is stored a sequence of instructions for performing the spectrum processing and computation operations described in this description. These instructions can be backed up on a storage medium, readable by the processor, of hard disk, CDROM or other memory type. The processor can be linked to a display unit 24, for example a screen.

Figure 2A:
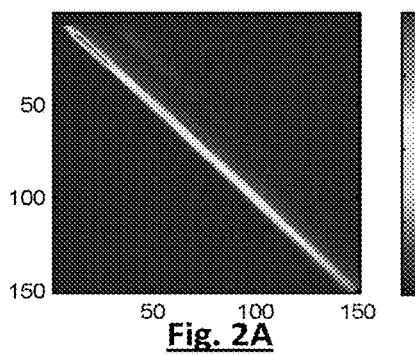
FIG. 2A represents a detector response matrix.

The detector can be characterized by a detector response matrix D, representing the imperfections of the detection. This matrix, of size N×N, N designating the number of channels of each spectrum formed by the detector, is represented in FIG. 2A. In this example, N=150, but, generally, the number of channels is greater than 2, even greater than 10, and can reach several thousand. Each term D(u, v) of this matrix represents a probability that a photon incident on the detector, of energy v, is considered by the detector as having an energy u.

Figure 2B:
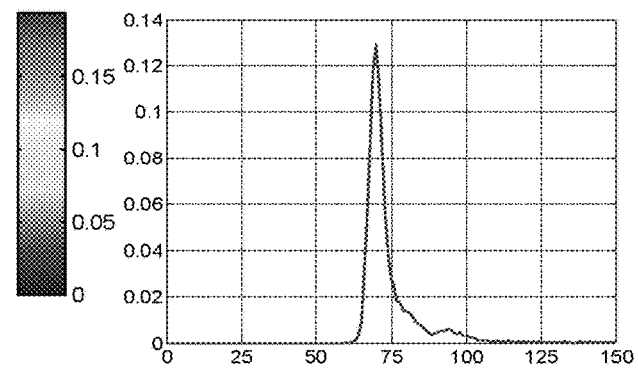
FIGS. 2B and 2C respectively represent a row and a column of this response matrix.
Figure 2C:
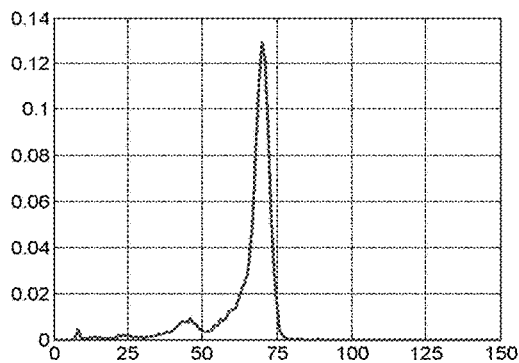

In other words, each row D(u, •) of the matrix, such as that represented in FIG. 2B, corresponds to a distribution of probability of the energy v of a photon reaching the detector when a photon of energy u is detected. FIG. 2B represents the row 70 of the matrix D. Similarly, each column D(•, v) of the matrix, such as that represented in FIG. 2C, represents a distribution of probability of the energy u detected by the detector when the photon reaching the detector has an energy v. FIG. 2C represents the column 70 of the matrix D. The finer the energy resolution of the detector, the more this matrix tends towards a diagonal matrix. In the case of a perfect detector, the matrix D is the identity matrix.

Figure 3:
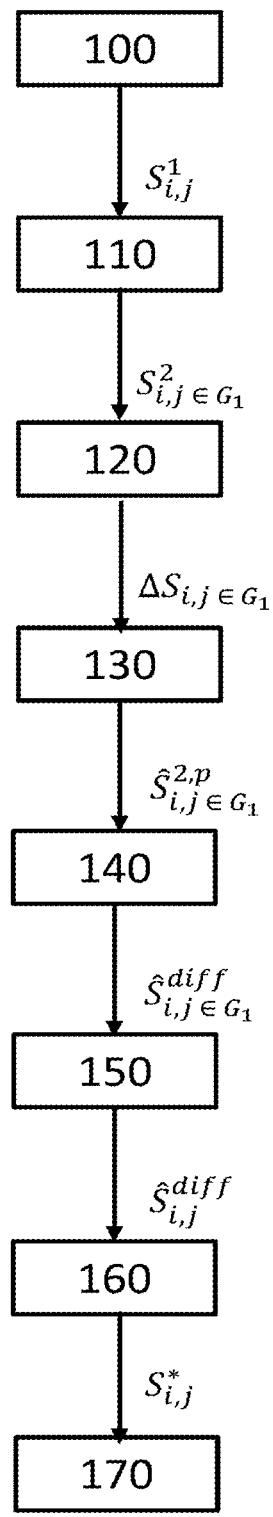
FIG. 3 represents the main steps of an embodiment of the invention.

There now follows a description of the main steps of a method according to a first embodiment of the invention, with reference to FIG. 3.

Step 100: acquisition of a first spectrum. The mask 15 is interposed between the source 11 and the detector 20. Each pixel $20_{i,j}$ is exposed to a radiation $I^1$, called first radiation, transmitted by the object in the presence of the mask, and acquires a spectrum therefrom, called first spectrum, $S_{i,j}^1$. The pixels $20_{i,j \in G1}$, situated in the extension of the attenuating elements $15_x$, belong to the first group $G_1$ and detect a radiation that is attenuated relative to the other pixels $20_{i,j \notin G_1}$. The first spectrum acquired by the pixels of the first group is denoted $S_{i,j \in G_1}^1$. The first spectrum acquired by the pixels not belonging to the first group is denoted $S_{i,j \notin G_1}^1$.

Step 110: obtaining, for each pixel $20_{i,j \in G_1}$ of the first group $G_1$, of a second spectrum $S_{i,j \in G_1}^2$ representative of a second radiation $I^2$ transmitted by the object without mask interposed between the source and the object. This second spectrum can be obtained experimentally, according to the configuration represented in FIG. 1B, the mask 15 being removed. This second spectrum can also be obtained by an estimation, from the first spectra $S_{i,j \notin G_1}^1$ not belonging to the first group $G_1$, and receiving a radiation not attenuated by the attenuating elements. This estimation can be made by interpolation, for example a linear or polynomial interpolation. It makes it possible to estimate the second spectrum $S_{i,j \in G_1}^2$ received by the pixels of the first group, in the absence of mask, without having to perform an experimental measurement.

According to another embodiment, detailed later, in relation to FIGS. 5A and 5B, each measurement has a corresponding measurement configuration C, representative of the position of the detector and/or of the source with respect to the object. This measurement configuration C changes between two successive measurements. The second spectrum $S_{i,j \in G_{1,C}}^{2,C}$ received by a pixel of the first group of the detector, according to a configuration C, can be estimated from a first spectrum $S_{i,j \notin G_{1,C'}}^{1,C'}$, produced in another configuration C', in which said pixel is not in the extension of an attenuating element and does not belong, in this other configuration, to the first group $G_{1,C'}$. This particular case is explained in more detail later, in the description of FIGS. 5A and 5B.

Step 120: for each pixel $20_{i,j \in G_1}$ of the first group $G_1$, determination of a so-called comparison spectrum $\Delta S_{i,j \in G_1}$, obtained by a comparison, for the same pixel, between the first spectrum $S_{i,j \in G_1}^1$ and the second spectrum $S_{i,j \in G_1}^2$. For example, the comparison is a subtraction, in which case $\Delta S_{i,j \in G_1} = S_{i,j \in G_1}^2 - S_{i,j \in G_1}^1$ (2). Subtracting spectra should be understood to mean subtraction of the content of each channel, of vector subtraction type.

Step 130: estimation of a so-called primary spectrum $\hat{S}_{i,j \in G_1}^{2,p}$ for each pixel of the first group, without a mask arranged between said pixel and the source. Such a spectrum represents the primary component of the second spectrum $S_{i,j \in G_1}^2$ reaching a pixel of the first group $G_1$. This estimation is made, for each pixel of this group, by considering the comparison spectrum $\Delta S_{i,j \in G_1}$ determined in the step 120, through the matrix product:

$$\hat{S}_{i,j \in G_1}^{2,p} = M \times \Delta S_{i,j \in G_1} \quad (3)$$

M is a transition matrix, previously determined, establishing a link between the comparison spectrum, determined in the step 120, and an estimation $\hat{S}_{i,j \in G_1}^{2,p}$ of the primary component of the radiation $I^2$ reaching the pixel $20_{i,j \in G_1}$ of the first group in the absence of a mask.

This estimation constitutes an important aspect of the invention. Its source lies in explaining the spectra $S_{i,j \in G_1}^1$, $S_{i,j \in G_1}^2$ measured by a pixel $20_{i,j \in G_1}$ of the first group respectively with and without mask. It is based on an assumption whereby the change of spectrum of the scattered radiation $S_{i,j \in G_1}^{diff}$, with or without mask, is negligible. Its validity is therefore conditional on the use of an attenuating and non-scattering mask as previously described.

Using the expression (1), $S_{i,j \in G_1}^1$ can be expressed in the form:

$$S_{i,j \in G_1}^1 = S_{i,j \in G_1}^{1p} + S_{i,j \in G_1}^{1diff} \quad (4),$$

$S_{i,j \in G_1}^{1p}$ and $S_{i,j \in G_1}^{1diff}$ respectively representing the direct and scattering spectra of the spectrum $S_{i,j \in G_1}^1$.

$$S_{i,j \in G_1}^{1p} = D \times (S^0 \circ e^{-att10 - att15}) \quad (5)$$

where: D designates the detector response matrix, previously described, $S^0$ designates the spectrum of the incident radiation $I^0$, $att_{10}$ and $att_{15}$ respectively designate the attenuation of the radiation reaching the pixel $20_{i,j}$ in the object 10 and in the mask 15 at each energy of the spectrum. $att_{10} = \Sigma_q l_q \mu_q$, and $att_{15} = l_{15x} \mu_{15x}$ where $l_q$ is the length traveled in each element $10q$ of the object 10, $\mu_q$ is a vector of linear attenuation coefficients, at each energy of the spectrum, of each element $10q$, $l_{15x}$ is the length traveled in the attenuating element $15_x$ conjugated with the pixel $20_{i,j}$ and $\mu_{15x}$ is a vector of linear attenuation coefficient at each energy of the spectrum. x designates the matrix product and ∘ is the Hadamard product. A linear attenuation coefficient $\mu_q$ bears out the following definition:

$$l_q \mu_q(E) = -\ln\left[\frac{I^q(E)}{I^{0,q}(E)}\right],$$

$I^{0,q}$ and $I^q$ respectively designating the radiation incident on and transmitted by an element $10q$ of the object of thickness $l_q$. Such a linear attenuation coefficient, known to those skilled in the art, depends on the energy and the materials constituting the element $10q$.

$$S_{i,j \in G_1}^2 = S_{i,j \in G_1}^{2p} + S_{i,j \in G_1}^{2diff} \quad (6),$$

with $$S_{i,j \in G_1}^{2p} = D \times (S^0 \circ e^{-att10}) \quad (7)$$

because the spectrum $S_{i,j\in G_1}{}^2$ corresponds to an acquisition without attenuating screen 15.

Therefore:

$$\Delta S_{i,j\in G_1} = S_{i,j\in G_1}{}^2 - S_{i,j\in G_1}{}^1 = D\times(S^0\circ e^{-att_{10}-att_{15}}) + D\times (S^0\circ e^{-att_{10}-att_{15}}) \quad (8)$$

because, by assumption, $S_{i,j\in G_1}{}^{2diff} = S_{i,j\in G_1}{}^{1diff}$.

Therefore $\Delta S_{i,j\in G_1} = D\times[(1-e^{-att_{15}})\circ(S^0\circ e^{-att_{10}})] \quad (9)$, 1 is a vector comprising only 1.

hence $\Delta S_{i,j\in G_1} = D\times[(1-e^{-att_{15}})\circ S_{i,j\in G_1}{}^{2p}] \quad (10)$ therefore $\Delta S_{i,j\in G_1} = D\times w S_{i,j\in G_1}{}^{2p} \quad (12)$ with $w = (1-e^{-att_{15}}) \quad (13)$.

It is possible to construct a square matrix, denoted $W^{-1}$, of size N by N, the terms of this matrix not being situated on the diagonal being nil, and each term n of the diagonal having the value $$W^{-1}(n,n) = \frac{1}{(1-e^{-att_{15}(n)})},$$

(14) where $att_{15}(n)$ designates the attenuation of the screen 15 at the energy corresponding to the channel of rank n. The index n designates the rank of a channel of the spectrum, which can be likened to an energy value E. The attenuation corresponds to the thickness of an attenuating element multiplied by the linear attenuation coefficient of the material constituting the attenuating material.

Thus, according to the expressions (13) and (14), having determined, for a pixel $20_{i,j\in G_1}$, the comparison spectrum $\Delta S_{i,j\in G_1}$, it is possible to estimate the primary spectrum $\hat{S}_{i,j\in G_1}{}^{2p}$ using the detector response matrix D and the matrix $W^{-1}$ previously defined, according to the expression:

$$\hat{S}_{i,j\in G_1}{}^{2p} = D\times W^{-1}\times D^{-1}\times \Delta S_{i,j\in G_1} \quad (15)$$

This expression can be rewritten as follows:
$\hat{S}_{i,j\in G_1}{}^{2p} = M\times \Delta S_{i,j\in G_1}$, which corresponds to the expression (3) written previously.

Where M is a transition matrix, such that $$M = D\times W^{-1}\times D^{-1} \quad (17)$$

The transition matrix M, generated from the detector response matrix D and from a matrix taking into account the attenuation of the mask 15, makes it possible to estimate the primary spectrum $\hat{S}_{i,j\in G_1}{}^{2p}$ of a radiation reaching, without attenuation, a pixel $20_{i,j\in G_1}$ of the first group, from a comparison ($\Delta S_{i,j\in G_1}$) between the spectra respectively determined with attenuation ($S_{i,j\in G_1}{}^1$) and without attenuation ($S_{i,j\in G_1}{}^2$). In this example, the comparison is a difference between these two spectra. The use of this transition matrix is an important element of the invention because it makes it possible to work back analytically to an estimation of the primary spectrum without attenuation from the comparison spectrum $\Delta S_{i,j}$.

The transition matrix M can be determined analytically but the inventors have proposed a method that makes it possible to estimate it experimentally, described hereinbelow.

Step 140: estimation of the scattered spectrum $\hat{S}_{i,j\in G_1}{}^{diff}$ for each pixel $20_{i,j\in G_1}$ of the first group.

With the spectrum $\hat{S}_{i,j\in G_1}{}^{2p}$ being estimated for each pixel $20_{i,j\in G_1}$ of the first group, from M and from $\Delta S_{i,j\in G_1}$, it is possible to estimate the scattering spectrum affecting each pixel $20_{i,j\in G_1}$ of this group, by using (6):

$$\hat{S}_{i,j\in G_1}{}^{2diff} = \hat{S}_{i,j\in G_1}{}^{1diff} = \hat{S}_{i,j\in G_1}{}^{diff} = S_{i,j\in G_1}{}^2 - \hat{S}_{i,j\in G_1}{}^{2p} \quad (18).$$

Step 150: estimation of the scattered spectrum $\hat{S}_{i,j\in G_1}{}^{diff}$ for each pixel $20_{i,j}$ of the detector. Having estimated the scattering spectrum of each pixel $20_{i,j\in G_1}$ of the first group, an assumption according to which the spatial change of the scattered radiation is of low frequency is used as a basis. In other words, the fluctuation of the spectrum of the scattered radiation from one pixel to another neighbouring pixel does not change abruptly. It is then possible to estimate the scattering spectrum $\hat{S}_{i,j}{}^{diff}$ of all the pixels of the detector by interpolation of the scattered spectra $\hat{S}_{i,j\in G_1}{}^{diff}$ of the pixels of the first group $G_1$. For the pixels not in the first group, the scattering spectrum is naturally the same with and without mask, since these pixels are not subjected to the attenuation of the mask.

Prior to the interpolation, some optional preprocessing operations can be performed. Take $20_{i,j\in k}$ as the pixels arranged in the shadow of the same attenuating element $15_k$. These pixels form a kernel k of which one pixel $20_k$, called central pixel of the kernel k, constitutes the centre. It is possible to estimate a scattering spectrum $\overline{S}_k{}^{diff}$ representative of this kernel and assign it to the central pixel. This spectrum representative of the kernel k is such that $$\overline{S}_k^{diff} = \frac{1}{C_k}\sum_{20_{i,j,\in k}} \hat{S}_{i,j}^{diff}, \quad (19)$$

where $C_k$ designates the number of pixels of the kernel k. The spectrum $\overline{S}_k{}^{diff}$ represents a mean of the estimations of the scattering spectra of the pixels of the kernel k. The interpolation can be performed by considering each spectrum $\overline{S}_k{}^{diff}$ representative of each kernel k.

Another optional preprocessing operation consists in a scaling of each spectrum $\overline{S}_k{}^{diff}$ representative of each kernel k, based on an assumption according to which the scattering spectrum reaching all the pixels of the detector has the same form, that is to say is similar from one pixel to another. This assumption is justified all the more so when the surface area of the detector is small, typically a few cm² or less. This scaling consists in applying a scalar $a_{k,n}$ to each channel n of a scattering spectrum $\overline{S}_k{}^{diff}$ representative of a kernel k, this scalar being determined according to the expression:

$$a_{k,n} = \underset{a}{\operatorname{argmin}}\left[a\left(\frac{1}{K}\sum_{k=1}^{k=K}\overline{S}_k^{diff}(n)\right) - \overline{S}_k^{diff}(n)\right]^2 \quad (20)$$

K represents the number of kernels k. It is then possible to adjust the spectrum $\overline{S}_k{}^{diff}$ representative of the scattering in each kernel k in such a way as to obtain an adjusted spectrum, denoted $\overline{\overline{S}}_k{}^{diff}$ with, for each channel n, $$\overline{\overline{S}}_k^{diff}(n) = \frac{a_{k,n}}{K}\sum_{k=1}^{k=K}\overline{S}_k^{diff}(n). \quad (21)$$

With the pixels of the detector being arranged in two dimensions XY, the interpolation is done, according to the variants used, on the basis of the spectra $\hat{S}_{i,j}{}^{diff}$, $\overline{S}_k{}^{diff}$ or $\overline{\overline{S}}_k{}^{diff}$ in a direction X, then in the other direction Y, or simultaneously, in both directions X and Y. The interpolation is performed energy channel by energy channel. It can be polynomial. In the example considered, the detector comprises 64*640 pixels. The interpolation is performed according to a $4^{th}$ order polynomial on each row of 640 pixels, then according to a second order polynomial on each column of 64 pixels.

Step 160: correction of the second spectrum $S_{i,j}^2$ (or of the first spectrum $S_{i,j}^1$, for the pixels not belonging to the first group) for all or some of the pixels $20_{i,j}$ of the detector, so as to obtain a corrected spectrum $S^*_{i,j}$, representative of the spectrum of the primary radiation transmitted by the object. In other words, if $S_{i,j}^p$ designates the spectrum of a primary radiation transmitted by the object onto the pixel $20_{i,j}$, $S^*_{i,j} = \hat{S}_{i,j}^p$.

This step is done simply, by a subtraction, for each pixel $20_0$, of the estimation of the scattered spectrum $\hat{S}_{i,j}^{diff}$ from the second spectrum (or from the first spectrum for the pixels not belonging to the first group).

Thus, for the pixels $20_{i,j \in G_1}$ of the first group:

$$S^*_{i,j} = \hat{S}_{i,j}^p = S_{i,j}^2 - \hat{S}_{i,j}^{diff} \quad (22)$$

and for the pixels $20_{i,j \notin G_1}$ not belonging to the first group:

$$S^*_{i,j} = \hat{S}_{i,j}^p = S_{i,j}^2 - \hat{S}_{i,j}^{diff} = S_{i,j}^1 - \hat{S}_{i,j}^{diff} \quad (22')$$

There is then obtained, for each pixel of the detector, a spectrum $S^*_{i,j}$ representing an estimation of the spectrum of the primary radiation transmitted by the object. It is then possible to obtain an image Im(E) representing the intensity of the primary radiation detected by each pixel, and at one or a plurality of energies (E), hence the designation spectral image. It is on the basis of this spectral image that the measurement is interpreted.

In the case of a tomographic reconstruction, the method is implemented in different configurations C, as previously described, each configuration having a corresponding spectral image or a plurality of corresponding spectral images $Im^C(E)$, on the basis of which the tomographic reconstruction is produced.

Whatever the embodiment, different channels E can be grouped together to constitute spectral bands $\Delta E$. It is then possible to obtain an image Im($\Delta E$) for each of these spectral bands.

Establishing the Transition Matrix.

One of the key elements of the invention is the transition matrix M used in the step 130. This matrix can be obtained by computation, according to the expression (17). However, the inventors have estimated that it is preferable to establish the transition matrix experimentally. Each row M(c, n) of the matrix M can be considered as a function inducing a deformation on either side of the diagonal term M(c, c), the latter being such that $$M(c,c) = \frac{1}{(1 - e^{-att_{15}(c)})} \quad (25)$$

Thus, each term of the row M(c, n) can be explained according to the expression:

$$M(c,n) = \frac{1}{(1 - e^{-att_{15}(c)})} \times f(c, n, \alpha_1 \ldots \alpha_p), \quad (26)$$

where $f$ is a deformation function and $\alpha_1 \ldots \alpha_p$ being parameters of the deformation function $f$.

Establishing the transition matrix entails defining an analytical expression of the deformation function $f$. For that, simulations are performed according to different calibration configurations, each calibration configuration Calib corresponding to a material of known nature and thickness. These configurations constitute a calibration base. For each calibration configuration Calib, the following steps are performed, described in relation to FIG. 4C, by considering a plurality of pixels of the detector belonging to the first group $G_1$:

Step 90 selection of an analytical form of the function $f$, parameterized by a set of parameters $(\alpha_1 \ldots \alpha_p)$;

Step 92 for each calibration configuration Calib, determination, by simulation, of a spectrum of the primary radiation $S_{i,j \in G_1}^{Calib,p}$;

Step 94: for each configuration, determination, by simulation or measurement, of a spectrum of the radiation reaching the detector with and without mask, and computation of a comparison spectrum $\Delta S_{i,j \in G_1}^{Calib,p}$, representing a difference between these two spectra;

Step 96: by using the spectra $S_{i,j \in G_1}^{Calib,p}$ corresponding to the different calibration configurations, determination of the set of parameters $(\alpha_1 \ldots \alpha_p)$ according to the expression:

$$(\alpha_1 \ldots \alpha_p) = \underset{(\alpha_1 \ldots \alpha_p)}{\operatorname{argmin}} \psi\left(S_{i,j \in G_1}^{Calib,p}; \hat{S}_{i,j \in G_1}^{Calib,p}\right) \quad (27)$$

where:

$\hat{S}_{i,j \in G_1}^{Calib,p}$ is an estimation of the primary spectrum $S_{i,j \in G_1}^{Calib,p}$ obtained by implementing the transition matrix M, parameterized by the parameters $(\alpha_1 \ldots \alpha_p)$ according to the expression: $\hat{S}_{i,j \in G_1}^{Calib,p} = M \times \Delta S_{i,j \in G_1}^{Calib}$ and $\psi$ is a function representative of an error, between the set of the spectra $S_{i,j \in G_1}^{Calib,p}$ and their respective estimations $\hat{S}_{i,j \in G_1}^{Calib,p}$ obtained using the transition matrix M, the latter being parameterized by the parameters $(\alpha_1 \ldots \alpha_p)$. It can be a function of quadratic error type.

Step 98: obtaining of the matrix M by using the function $f$ the parameters of which have been determined in the step 96, and by using the expression (26).

Other Embodiments

According to one embodiment, detailed in relation to FIGS. 5A and 5B, the position of the detector and/or of the source with respect to the object changes between two consecutive measurements. Also, each measurement has a corresponding configuration C, each configuration being characterized by a relative position of the detector 20 and/or of the source 11 in relation to the objet 10, as previously defined. Each configuration is characterized by a parameter $P_C$, the latter representing the position of the detector and/or of the source in relation to the object. This parameter can be a scalar or a vector. In the examples represented in FIGS. 5A and 5B, the source is fixed relative to the detector and the assembly consisting of the source and the detector revolves around the object, on an axis Y at right angles to the plane XZ, at an angle $\theta$ relative to an initial position. This angle constitutes the parameter of each measurement configuration $P_C$.

In a first configuration C, represented in FIG. 5A, $\theta=0$. The pixel $20_i$ is masked by an attenuating element $15_x$ of the mask 15. In a second configuration C', represented in FIG.

5B, $\theta=\theta'>0$. The pixel $20_l$ is not masked by the mask 15. In such an embodiment, for the pixel 1, the first spectrum $S_l^{1,C}$ is obtained according to the configuration C represented in FIG. 5A, whereas the second spectrum $S_l^{2,C}$ corresponds to the first spectrum $S_l^{2,C'}$ obtained according to the configuration C'. In other words, $S_l^{2,C}=S_l^{1,C'}$. This embodiment makes it possible to retain a fixed mask between the source and the object, the second spectrum $S_{i,j}^{2,C}$ of a pixel $20_{i,j}$ being obtained upon the measurement of the first spectrum $S_{i,j}^{1,C'}$ of the configuration C'. In the first configuration C, the pixel $20_{i,j}$ belongs to the first group $G_{1,C}$, whereas, in the second configuration C', this pixel does not belong to the first group $G_{1,C'}$.

Preferably, these two configurations are sufficiently comparable for the spectrum measured by the pixel $20_l$, in the second configuration, to be representative of the radiation, without mask, in the first configuration. Thus, preferably, the parameters P and P' respectively associated with the configurations C and C' are close. Close should be understood to mean that their relative deviation does not exceed a predetermined threshold, for example 10 or 20%.

According to one embodiment, the method is implemented according to a plurality of configurations C, each configuration having an associated position of the detector and of the source in relation to the object, so as to obtain, in each configuration, for a plurality of pixels, a corrected spectrum $S^*_{i,j}{}^{,C}$. The corrected spectra $S^*_{i,j}{}^{,C}$ associated with each configuration $S^*_{i,j}{}^{,C}$ are used to produce a tomographic reconstruction of the object 10. Each configuration can be parameterized by a parameter $P^C=\theta^C$, representing an angle formed by the source-detector assembly and the object.

The reconstruction notably aims to reconstruct the form of the elements $10q$ forming the object, and their linear attenuation coefficient $\mu_q$ or any other coefficient expressing an attenuation. It is produced by implementing known inversion algorithms, on the basis of the spectral images $Im^C(E)$ corresponding to each energy E, each image representing a quantity of radiation at said energy, this quantity being obtained according to the corrected spectra $S^*_{i,j}{}^{,C}$. The use of these corrected spectra makes it possible to significantly improve the quality of the tomographic reconstruction, as described in the examples which follow.

Prior to the reconstruction, it is possible to proceed with a grouping together of spectra in spectral bands $\Delta E$, typically of a few tens of keV, in order to form spectra $S^*_{i,j}{}^{,C}(\Delta E)$ in each of these spectral bands, and obtain spectral images $Im^C(\Delta E)$ corresponding to spectral bands.

EXAMPLES

There now follows a description of the exemplary embodiments of the invention, based on simulations performed by computation code, according to an application in radiography and an application in tomography. First, an example of establishing a transition matrix M is described.

As described in relation to FIG. 4C, a transition matrix is determined using a calibration base, comprising one or more materials. In this example, two materials (water and aluminium) are considered, the thicknesses considered being:
- for the aluminium, between 0 and 0.2 cm according to a pitch of 0.1 cm;
- for the water, between 0 and 20 cm, according to a pitch of 0.5 cm.

The analytical form of the function $f$ is chosen such that:

$$\text{for } n \geq c, f(c, n, \alpha_1, \alpha_2) = 0.9 e^{-\frac{(n-c)^2}{2\alpha_1^2}} + 0.1 e^{-\alpha_2 n} \quad (30)$$

$$\text{for } n < c, f(c, n, \alpha_1, \alpha_2) = e^{-\frac{(n-c)^2}{2\alpha_1^2}} \quad (31)$$

The indices c and n are respectively associated with a row and with a column of the transition matrix.

Moreover, for each calibration configuration, the primary spectrum $S_{i,j\in G_1}^{Calib,p}$ reaching the pixels of the first group of the detector implemented was modelled and simulated measurements of the spectrum were performed with and without mask, so as to form a comparison spectrum $\Delta S_{i,j\in G_1}^{Calib}$. The values $\alpha_1$ and $\alpha_2$ were then determined as previously described. The result was $\alpha_1=0.2$ and $0.04 \leq \alpha_2 \leq 0.18$. FIG. 4A represents the transition matrix M obtained, whereas FIG. 4B represents a column of this matrix of coordinate n=45.

There now follows a description of the simulations implementing the device represented in FIGS. 1A and 1B. The object is a phantom simulating the trunk of a human being. It comprises a matrix $10_0$, the section of which, in a plane parallel the plane XZ, is oval, the greatest dimensions on the axes Z and X being respectively 20 cm and 40 cm. This matrix $10_0$ represents the body and is made up of water. A first element $10_1$ and a second element $10_2$ arranged within the matrix $10_0$, represent the lungs. Their section, in a plane parallel to the plane XZ, is oval, the greatest dimensions on the axes Z and X being respectively 11 cm and 15 cm. These elements consist of air. A third element $10_3$ represents the spinal column. Its section, in a plane parallel to the plane XZ, is in the form of a disc of 3 cm diameter. A fourth element $10_4$, of rectangular form, represents a vertebra. Its constituent material is a bone, modelled according to an ICRU (International Commission on Radiation Units and Measurements) database. Finally, the periphery of the matrix $10_5$ consists of an annular bone of oval section, representing the dimensions. Its thickness is 1 cm. Substantially spherical inclusions $10_7$, $10_8$ and $10_9$ of 2 cm diameter are arranged at the level of the first and second elements, representing the lungs. These inclusions consist of PMMA (polymethylmethacrylate) and represent cancerous tumours.

The irradiation source 11 is an X-ray tube with a tungsten anode, subjected to a voltage of 110 kV. The detector 20 comprises 640 pixels (on the X axis)*64 pixels (on the Y axis), each pixel comprising a thickness of CdTe of 5 mm. The surface area of each pixel, in the plane XY on which the detector extends, is 1 mm*1 mm. The detector is energy-resolved, and each pixel makes it possible to obtain spectra according to 1 keV energy channels. The mask 15 used is that represented in FIG. 2.

FIGS. 6A, 6B and 6C respectively represent the total radiation without the mask, the primary radiation and the primary radiation estimated by implementing the invention, according to the method represented in FIG. 3, over all of the pixels of the detector. During the implementation of the method, the second spectra $S_{i,j \in G_1}^2$ are obtained by simulating a mask, as represented in FIG. 2, placed at a distance of 10 cm from the source. The quantity represented, according to the colour code, corresponding to each pixel $20_{i,j}$ is a value of the attenuation $A_{i,j}$, such that $$A_{i,j} = -\log\left(\frac{\sum_n n S'_{i,j}(n)}{\sum_n n S^0_{i,j}(n)}\right) \quad (32)$$

where:
- $S_{i,j}^0$ is a spectrum measured by a pixel $20_{i,j}$ when the detector is directly exposed to the source. That represents the spectrum of the incident radiation $I^0$.
- $S'_{i,j}$ is a spectrum of interest measured by a pixel $20_{i,j}$. In FIG. 6A, $S'_{i,j}$ represents the spectrum of the radiation transmitted by the object, without the mask: $S'_{i,j} = S_{i,j}$. In FIG. 6B, $S'_{i,j}$ represents the primary spectrum of the radiation transmitted by the object, without the mask, the object being arranged between the source and the detector: $S'_{i,j} = S_{i,j}^P$. In FIG. 6C, $S'_{i,j}$ represent the spectrum corrected according to the invention, which corresponds to an estimation of the primary spectrum of $S_{i,j}$: $S'_{i,j} = S^*_{i,j} = \hat{S}_{i,j}^P$.

Each quantity $A_{i,j}$ is representative of a global attenuation in the object, the term global describing the fact that it is determined for all the energy channels of the spectrum. That allows for a representation of each spectrum of interest $S'_{i,j}$ by a scalar, which simplifies the illustrations. FIGS. 6A, 6B and 6C show that:
- the estimation of the spectrum of the primary radiation $\hat{S}_{i,j}^P$, implementing the invention (FIG. 6C) is consistent with the spectrum of the primary radiation modelled $S_{i,j}^P$ (FIG. 6B);
- The spectra of the primary radiation show greater contrast (FIGS. 6B and 6C) than the spectrum of the total radiation (FIG. 6A). The separation of the spectrum of the primary radiation allows for a better spatial separation of zones exhibiting different attenuations. That is particularly visible in the central part of the images, corresponding to the dense elements $10_3$ and $10_4$ (bone). The recourse to the spectrum of the primary radiation makes it possible to obtain an attenuation value closer to reality.

These results are confirmed in FIG. 6D, representing a central profile of each of these images according to one and the same value of y=32. In this figure, the indices A, B and C refer respectively to the FIGS. 6A, 6B and 6C.

Figure 7A:
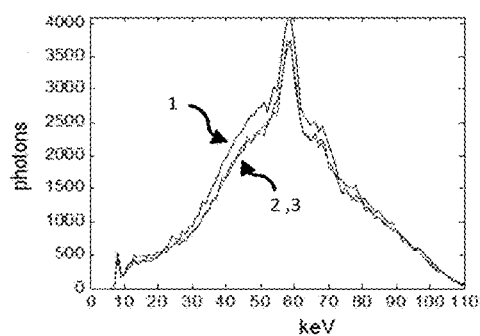
Figure 7B:
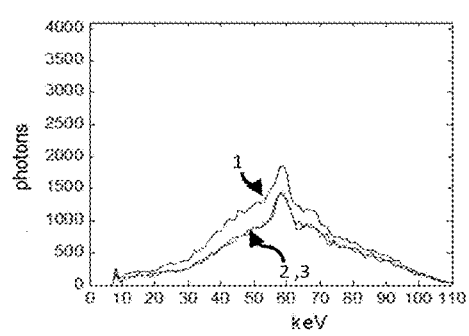
Figure 7C:
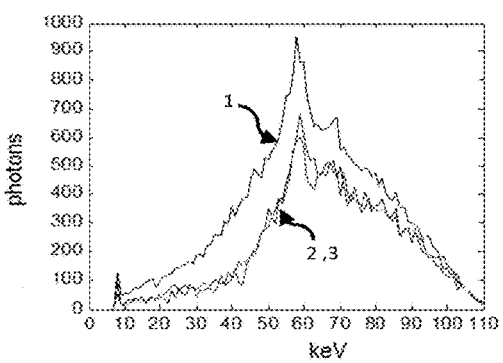
Figure 7D:
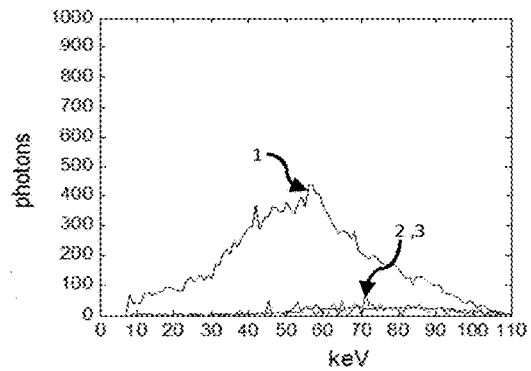

FIGS. 7A, 7B, 7C and 7D represent the spectra of the total radiation $S_{i,j}$, of the modelled primary radiation $S_{i,j}^P$ and of the estimated primary radiation $\hat{S}_{i,j}^P$ according to the invention, respectively on the pixels $20_{i,j}$ of the detector of coordinates (i=100, j=15; i=192, j=38; i=32, j=55; i=320, j=32). In each of these figures, the indices 1, 2 and 3 respectively represent the spectrum of the total radiation $S_{i,j}$, the spectrum of the modelled primary radiation $S_{i,j}^P$ and the spectrum of the primary radiation $\hat{S}_{i,j}^P$ estimated according to the invention. The consistency, at each of the points, between the spectra of the primary radiation modelled and estimated according to the invention will be noted. The pixel i=320, j=32, represented in FIG. 7D, is noteworthy in that almost all of the radiation detected is a scattered radiation, the contribution of the primary radiation being negligible. This pixel is placed face to face with the strongly attenuating bone elements $10_3$ and $10_4$. That means that the radiation measured by this pixel essentially consists of scattered radiation originating from the object. The interest and the effectiveness of the invention are measured here.

The effectiveness of a method for correcting the scattered spectrum is frequently measured by an indicator, denoted SPR, the acronym for Scatter-to-Primary-Ratio.

A first expression of this indicator, called integral expression, is such that:

$$SPR = \frac{\sum_n \sum_{i,j} nS_{i,j}(n)}{\sum_n \sum_{i,j} nS_{i,j}^P(n)} \times 100 \quad (33)$$

The term "integral" describes the fact that the indicator is based on all the pixels and energy channels.

This indicator can be pixelated, that is to say be associated with each pixel $20_{i,j}$ of the detector, in which case it is explained by a second expression, called spatial expression:

$$SPR(i,j) = \frac{\sum_n nS_{i,j}(n)}{\sum_n nS_{i,j}^P(n)} \times 100 \quad (34)$$

It can also be expressed as a function of the energy, over all of the pixels of the detector, in which case it is explained according to a third expression, called spectral expression:

$$SPR(n) = \frac{\sum_{i,j} nS_{i,j}(n)}{\sum_{i,j} nS_{i,j}^P(n)} \times 100 \quad (35)$$

Whatever its expression, integral, spatial or spectral, the lower the coefficient SPR, the smaller the share scattered respectively over all of the detector, in the pixel $20_{i,j}$, or in the energy range n.

It is also possible to quantify the effectiveness of the estimation of the spectrum of the primary radiation by a normalized differential indicator Ind_diff, reflecting the effectiveness of the estimation for each pixel $20_{i,j}$ of the detector. Like the coefficient SPR previously described, this indicator Ind_diff can be expressed in integral, spatial or spectral fashion, respectively according to the expressions:

$$\text{Ind\_diff} = \frac{\sum_n \sum_{i,j} n(|\hat{S}_{i,j}^P(n) - S_{i,j}^P(n)|)}{\sum_n \sum_{i,j} nS_{i,j}^P(n)} \times 100 \quad (36)$$

$$\text{Ind\_diff}(i,j) = \frac{\sum_n n(|\hat{S}_{i,j}^P(n) - S_{i,j}^P(n)|)}{\sum_n nS_{i,j}^P(n)} \times 100 \quad (37)$$

$$\text{Ind\_diff}(n) = \frac{\sum_{i,j} n(|\hat{S}_{i,j}^P(n) - S_{i,j}^P(n)|)}{\sum_{i,j} nS_{i,j}^P(n)} \times 100 \quad (38)$$

Whatever its expression, integral, spatial or spectral, the lower the coefficient Ind_diff, the better the estimation.

Table 1 represents, over all of the pixels of the detector, the different indicators described above:

TABLE 1

| | | Spatial | | | Spectral | | |
|---|---|---|---|---|---|---|---|
| | Integral | Min | Max | Mean | Min | Max | Mean |
| SPR | 19.5% | 7.10% | 1.06 × 10³% | 86.6% | 11.4% | 31.9% | 21.6% |
| Ind_diff | 4.31% | 2.20% | 88.2% | 10% | 2.64% | 8.36% | 4.75% |

In the image considered, the signal to primary integral ratio is close to 20%. It is found that the indicator Ind_diff remains on average very low, which attests to the good quality of the estimation.

A tomographic reconstruction of the object represented in FIG. 1 was produced, by simulating a rotation of the measurement device (source, mask, detector) about the object, the axis of rotation being parallel to the axis Z, and by performing an acquisition for each angular pitch of one degree. Before the reconstruction, the channels of the spectra are grouped together in four spectral bands of 21 keV width between 23 keV and 110 keV. These spectral bands are 23 keV-44 key; 45 keV-66 key; 67 keV-88 key; 89 keV-110 keV. FIGS. 8A, 8B and 8C represent a cross section of the object attenuation reconstructed, respectively on the basis:

of the spectrum of the total radiation $S_{i,j}$;

of the spectrum of the simulated primary radiation $S_{i,j}^P$;

of the spectrum of the primary radiation $\hat{S}_{i,j}^P$, estimated according to the invention, after having simulated, at each angular pitch, a measurement with and without mask.

Each spectrum was modelled according to a spectral resolution of 1 keV. Then, a channel grouping was performed, so as to obtain the four spectral bands previously described. The reconstruction according to each spectral band is represented in FIGS. 8A, 8B and 8C.

A good consistency will be noted between reconstructions produced on the basis of the simulated primary radiation and on the basis of the primary radiation estimated according to the invention. It can also be seen that the taking into account of the primary radiation has commensurately greater effect when the energy is low.

Experimental tests were carried out by using an anthropomorphic phantom representing the thorax of a person (Anthropomorphic thorax phantom). The experimental conditions are:

radiation source: x-ray tube YXLON Y.TU 160-D06—operating voltage 110 kV;

detector: 128×1 pixels MutliX ME 100 energy resolved CdTe detector—pitch 0.8 mm—thickness 3 mm. The linear detector was translated to acquire 2D images of 128×451 pixels;

mask consisting of an array of 11×21 aluminium cylinders, of 2 mm diameter and of 2 mm height, the distance between two adjacent cylinders being 5 mm;

The transition matrix M was established by using aluminium cylinders and PMMA (polymethylmethacrylate) of 2 cm diameter. The thickness of the aluminium cylinders varies between 0 cm and 16 cm by 4 cm increments. The thickness of the PMMA cylinders varies between 0 cm and 3 cm by 1 cm increments.

FIGS. 9A, 9B and 9C respectively represent an attenuation $A_{i,j}$, as described in relation to the equation (32), computed within an energy range 25 keV-110 keV, and computed on the basis:

of a spectrum of the transmitted radiation, measured by each pixel $20_{i,j}$ of a spectrum of the transmitted radiation from which has been subtracted an estimation of a scattered radiation. This estimation is made by placing an attenuating band, called Beam Stop. The pixels situated facing this attenuating band measure a spectrum representative of the scattered spectrum. This spectrum is then subtracted from the transmitted spectrum, so as to obtain an estimation of the primary spectrum for each pixel. This is a reference correction method.

of a spectrum of the primary radiation estimated according to the invention, on each pixel $20_{i,j}$.

A good consistency in FIGS. 9B and 9C can be observed, which attests to the validity of the correction according to the invention.

In FIG. 9B, a horizontal line has been represented. FIG. 9D represents a profile of the intensity on each of the FIGS. 9A to 9C, along this line. The good consistency between the profiles deriving from the FIGS. 9B and 9C can be observed. In this figure, the indices A, B and C refer respectively to the FIGS. 9A, 9B and 9C.

FIGS. 10A, 10B, 10C and 10D each represent the spectra of the transmitted radiation, corrected according to a reference method and corrected according to the invention, respectively on each point 1, 2, 3 and 4 represented in FIG. 9B. In each of these figures, the indices 1, 2 and 3 respectively represent the spectrum of the total radiation $S_{i,j}$, the spectrum of the primary radiation $S_{i,j}^P$ using the reference method, and the spectrum of the primary radiation $\hat{S}_{i,j}^P$ estimated according to the invention.

The invention will be able to be applied in spectral imaging methods implementing ionizing radiations, in particular X or gamma radiations, for medical applications or, more generally, in the non-destructive inspection of objects, aiming to investigate the internal structure of said object. The object can be, for example, luggage, an industrial product, a structural element of an installation, for example a pipeline, nuclear waste, etc.

The invention allows for an estimation of the primary component of a radiation, thus limiting the influence of the scattered radiation. The quality of the image obtained, and in particular the spatial resolution, is then improved. The result thereof is more accurate results, and results more conformal to the object examined.

The implementation of the method is simple and can be adapted to existing devices. Furthermore, the transition matrix can be established beforehand, which allows for a rapid implementation of the method, not requiring high computation time. The method is therefore suited to implementation at an industrial rate.

The invention claimed is:

1. A Method for correcting a spectrum of an ionizing electromagnetic radiation transmitted by an object, the object being arranged between an irradiation source and a detector, the irradiation source being configured to emit an ionizing electromagnetic radiation, called incident radiation, towards said object;

the detector comprising pixels, each pixel being configured to detect a radiation transmitted by the object towards the detector, and to acquire a spectrum therefrom, the transmitted radiation comprising a scattering radiation, caused by the scattering of the incident radiation in the object, and a primary radiation;

the method comprising the steps of:
- a) interposing a mask between the source and the object, and acquiring, by several pixels, a first spectrum of a first radiation transmitted by the object, the mask comprising attenuating elements, configured to attenuate a part of said incident radiation, and of which a projection on the detector defines a first group of pixels;
- b) obtaining, for each pixel of the first group of pixels, a second spectrum of a second radiation transmitted by the object to the detector, in the absence of said mask;
- c) comparing, for each pixel of said first group of pixels, the first spectrum and the second spectrum, so as to obtain a comparison spectrum;
- d) at each pixel of the first group of pixels, applying a transition matrix, previously established, to said comparison spectrum, to obtain an estimation of a so-called primary spectrum representing the primary radiation transmitted by the object to said pixel, and estimating a scattering spectrum, representative of the scattering radiation transmitted by the object;
- e) for all or some of the pixels of the detector, from each scattering spectrum estimated in the step d), correcting the second spectrum or the first spectrum, so as to obtain a corrected spectrum.

2. The method according to claim 1, in which the step e) comprises, prior to the correction, an estimation of a scattering spectrum for all of the pixels of the detector.

3. The method according to claim 1, in which the step e) comprises, for each pixel, a subtraction of the estimated scattering spectrum from the second spectrum or the first spectrum.

4. The method according to claim 1, in which, in the step b), for each pixel of the first group, the second spectrum is obtained:
- either by an acquisition of the second spectrum by said pixel;
- or by an estimation on the basis of at least one first spectrum acquired by at least one pixel not belonging to the first group.

5. The method according to claim 1, in which:
- the step a) is implemented in a plurality of configurations, each configuration being associated with a position of the detector and of the source relative to the object, so as to obtain, in each configuration and for each pixel, a first spectrum, each configuration also defining a first group of pixels;
- the step b) comprises, for all or some of the pixels of the first group defined by a configuration, a determination of a second spectrum from a first spectrum obtained according to another configuration.

6. The method according to claim 5, in which each configuration being associated with a parameter, such that at least one second spectrum according to a configuration associated with a first parameter is obtained from a first spectrum obtained according to another configuration, the latter being associated with a second parameter, different from the first parameter.

7. The method according to claim 6, in which said parameter is an angle of inclination of the source and/or of the detector relative to the object.

8. The method according to claim 1, in which, in the step d), the estimation of the primary spectrum comprises the matrix product of said transition matrix by each comparison spectrum.

9. The method according to claim 1, in which each attenuating element is configured to attenuate between 5% and 80% of the radiation to which it is exposed.

10. The method according to claim 1, in which, the mask extending along a surface, each attenuating element is distant from another attenuating element by a distance less than 1 cm.

11. The method according to claim 1, in which the steps a) to e) are implemented according to a plurality of configurations, each configuration having associated with it a position of the detector and of the source relative to the object, so as to obtain, in each configuration, for a plurality of pixels, a corrected spectrum, the corrected spectra of each configuration being used to produce a tomographic reconstruction of the object.

12. The method according to claim 1, in which the steps a) to e) are complemented by the steps of:
- f) selecting at least one energy or an energy range;
- g) producing an image, of which each pixel comprises a data obtained from a corrected spectrum, associated with a pixel of the detector, within the selected energy or in the selected energy range.

13. The method according to claim 12, in which, in the step g), each pixel of the image comprises an information item relating to an integral or to a mean of said corrected spectrum in said selected energy range.

14. The method according to claim 1, in which the mask is interposed between the irradiation source and the object.

15. The method according to claim 1, in which the transition matrix is obtained by performing a plurality of so-called calibration measurements, each calibration measurement being performed by interposing a material of known nature and thickness between the irradiation source and the detector.

16. An information storage medium, comprising instructions for the execution of steps c) to e) of the method according to claim 1, these instructions being configured to be executed by a microprocessor.

17. The Device for producing images of an object comprising:
- an irradiation source, configured to emit an ionizing electromagnetic radiation, called incident radiation, towards said object;
- a detector comprising pixels, each pixel being configured to detect a radiation transmitted by the object towards the detector, and to acquire a spectrum therefrom;
- a mask, able to be interposed between the source and the object, the mask comprising attenuating elements, configured to attenuate a part of the incident radiation, and of which a projection onto the detector defines a first group of pixels;
- a) a processor, configured to receive spectra detected by each pixel, and to implement steps c) to e) of the method of claim 1.

* * * * *